United States Patent [19]
Violante et al.

[11] Patent Number: 6,106,473
[45] Date of Patent: Aug. 22, 2000

[54] ECHOGENIC COATINGS

[75] Inventors: Michael R. Violante, Pittsford; Richard J. Whitbourne, Fairport; John F. Lanzafame, Rochester; Margaret Lydon, N. Chili, all of N.Y.

[73] Assignee: STS Biopolymers, Inc., Henrietta, N.Y.

[21] Appl. No.: 08/965,393

[22] Filed: Nov. 6, 1997

Related U.S. Application Data

[60] Provisional application No. 60/034,045, Nov. 6, 1996.

[51] Int. Cl.$^7$ .......................................................... A61B 8/00
[52] U.S. Cl. .......................................... 600/458; 427/2.11
[58] Field of Search ..................................... 600/458, 437; 424/9.5, 9.52; 427/2.11

[56] References Cited

U.S. PATENT DOCUMENTS

| | | |
|---|---|---|
| 3,695,921 | 10/1972 | Shepherd et al. . |
| 4,100,309 | 7/1978 | Micklus et al. . |
| 4,345,602 | 8/1982 | Yoshimura et al. . |
| 4,373,009 | 2/1983 | Winn . |
| 4,401,124 | 8/1983 | Guess et al. . |
| 4,456,017 | 6/1984 | Miles . |
| 4,459,317 | 7/1984 | Lambert . |
| 4,585,666 | 4/1986 | Lambert . |
| 4,589,873 | 5/1986 | Schwartz . |
| 4,642,267 | 2/1987 | Creasy et al. . |
| 4,682,607 | 7/1987 | Vaillancourt . |
| 4,721,117 | 1/1988 | Mar et al. . |
| 4,729,914 | 3/1988 | Kliment et al. . |
| 4,739,768 | 4/1988 | Engelson . |
| 4,769,013 | 9/1988 | Lorenz et al. . |
| 4,835,003 | 5/1989 | Becker . |
| 4,841,976 | 6/1989 | Packard et al. . |
| 4,867,174 | 9/1989 | Skribiski . |
| 4,884,579 | 12/1989 | Engelson . |
| 4,950,257 | 8/1990 | Hibbs et al. . |
| 4,991,602 | 2/1991 | Amplatz et al. . |
| 5,041,100 | 8/1991 | Rowland et al. . |
| 5,061,254 | 10/1991 | Karakelle et al. . |
| 5,069,226 | 12/1991 | Yamauchi et al. . |
| 5,201,314 | 4/1993 | Bosley et al. . |
| 5,331,027 | 7/1994 | Whitbourne . |
| 5,370,901 | 12/1994 | Tournier et al. . |
| 5,452,726 | 9/1995 | Burmeister et al. . |
| 5,580,575 | 12/1996 | Unger et al. . |
| 5,824,048 | 10/1998 | Tuch . |
| 5,853,745 | 12/1998 | Darouiche . |

FOREIGN PATENT DOCUMENTS

| | | |
|---|---|---|
| 90/03768 | 4/1990 | European Pat. Off. . |
| 04070965 A1 | 10/1990 | European Pat. Off. . |

OTHER PUBLICATIONS

Current Problems in Diagnostic Radiology, Percutaneous Transluminal Angioplasty, Charles J. Tegtmeyer, vol. XVI, No. 2, Mar./Apr. 1987.

McGraw–Hill Encyclopedia of Science & Technology, 6$^{th}$ Edition, (1987) C.R. Martinson, et al.; Surface Coating, vol. 18, p.7.

Interpenetrating Polymer Networks, Daniel Klempner, (1978).

Endovascular Surgery, Wesley S. Moore, M.D., et al. (1989 W.B. Saunders Company), pp. 157–159.

*Primary Examiner*—Francis J. Jaworski
*Attorney, Agent, or Firm*—Michael A. Gollin; Venable

[57] ABSTRACT

Coatings to enhance the echogenicity of materials are especially useful for medical devices wherein the practitioner desires to locate or visualize a device by ultrasonic imaging when the device is inserted into a body cavity. These coatings can be applied to any device of virtually any composition. To accomplish this, a polymer matrix is formed containing an entrapped gas in enclosed bubbles or open surface channels or cavities. Coated needles are visible in ultrasound when inserted in animals. A pre-coat or base coat may be applied to condition the surface to enhance adhesion. A finish coat or top coat may be applied to improve durability, smoothness, and biocompatibility, lubricity, antibiotic, antimicrobial, antithrombogenic activity, and other desirable properties for the finished product. Coating liquids and methods for preparing and applying such coatings are disclosed, including forming bubbles by chemical reaction during the coating process.

49 Claims, 4 Drawing Sheets

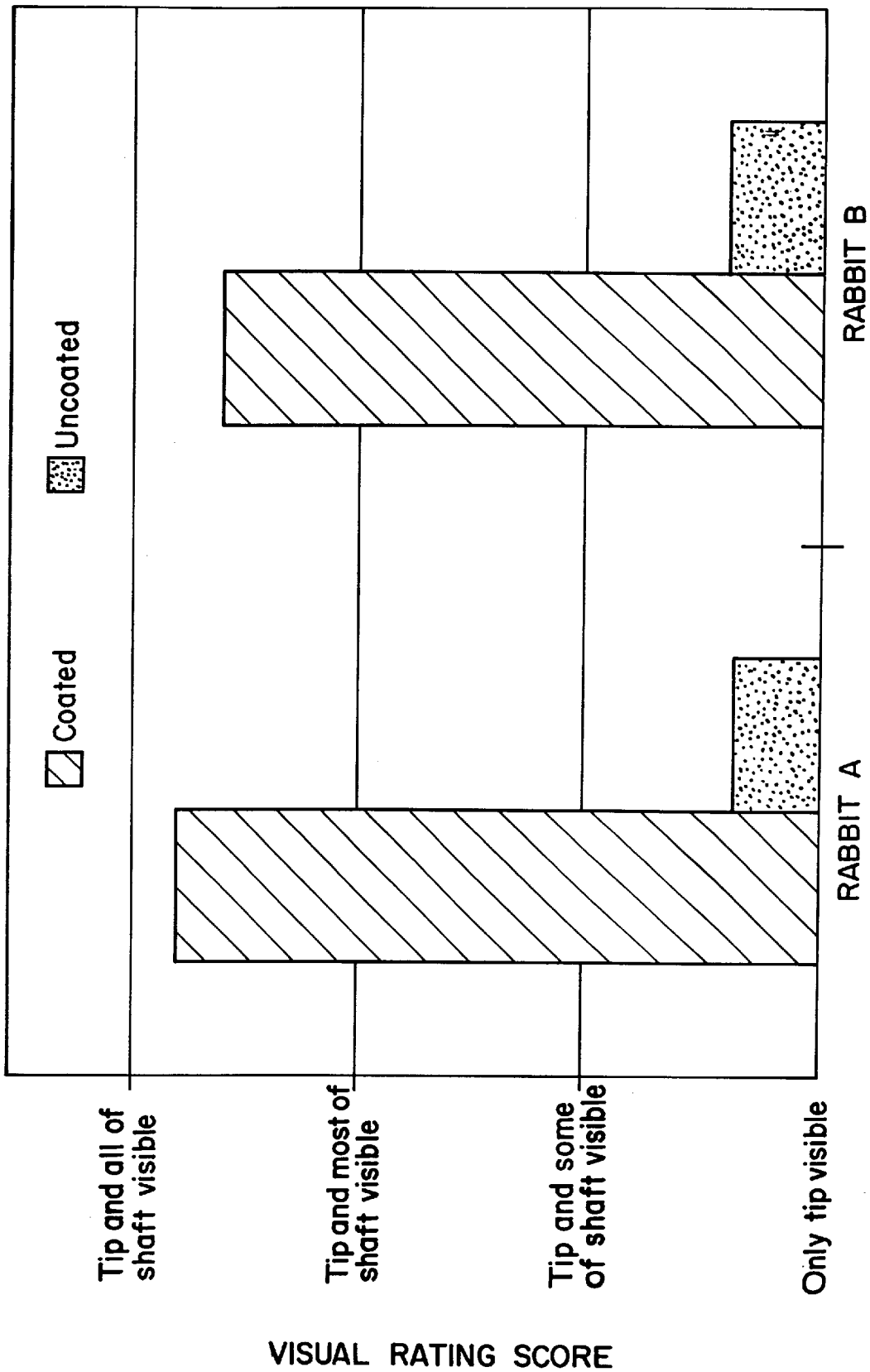

ECHOGENIC COATINGS

This application claims the benefit of provisional application 60/034,045, filed Nov. 6, 1996, which is incorporated herein by reference.

BACKGROUND OF THE INVENTION

1. Field of the Invention

This invention relates to echogenic coatings for biomedical devices, and methods of preparing them. The coatings include echogenic irregularities and dramatically improve the visibility of the devices when viewed using ultrasound imaging techniques.

2. Background Information

Ultrasonic imaging has many applications. This technology is especially valuable for medical imaging applications because diagnostic ultrasound procedures are safe, very acceptable to patients and less expensive than other digital imaging technologies such as CT or MRI. Also, instruments are widely available and images are produced in real time. However, currently the contrast resolution of ultrasound is not as good as the other technologies. Hence, improvements in image quality open the door to rapid growth of this technique.

A variety of ultrasound contrast agents are known. These include porous uniformly-sized non-aggregated particles as described in Violante and Parker, Ser. No. 08/384,193. Such contrast agents may enhance the visibility of target tissue into which they are injected, but they can not enhance the ultrasound visibility of insertable medical devices.

In many medical procedures, the ability to accurately place a device within a tissue or passageway, especially within a suspected lesion, such as an abscess, cyst, tumor, or in a specific organ such as kidney or liver, is very important to complete the diagnosis or therapy of a patient. Such devices include needles, catheters, stents, dilators, introducers, angiography and angioplasty devices, pacemakers, in-patient appliances such as pumps, and artificial joints. Fine needle biopsy, fluid drainage, catheter placement for angiography, angioplasty, amniocentesis, or drug delivery are a few examples of medical procedures requiring accurate placement of medical devices. Inaccurate device placement may create a need to repeat a procedure thereby adding to medical care costs and patient discomfort or may, in some cases, result in a false negative diagnosis for example if a biopsy needle missed a lesion. Worse, misplacement may harm a patient directly.

Most medical devices, including catheters, have an acoustic impedance similar to that of the tissue into which the device is inserted. Consequently visibility of the device is poor and accurate placement becomes extremely difficult if not impossible. Another problem affecting the visibility of devices is the scattering angle. For example, stainless steel needles have an acoustic impedance significantly different from tissue and are highly visible under ultrasound imaging when the needle is in the plane of the ultrasound beam, but if the needle is moved to some other angle off-axis, the ultrasound beam is scattered in a direction other than the transducer and the needle becomes less visible or even invisible under ultrasound imaging.

Both of the problems described above have been addressed by efforts to increase the scattering power of the device so that the device becomes visible even when it is not completely in the plane of the ultrasound beam. U.S. Pat. No. 4,401,124 describes enhancing the scattering power of a needle by means of grooves in the tip of the device. This approach improves the angle of echo scattering, but the intensity of the scattered signal is less than ideal, and at any angle other than the optimum, signals are lost into the background speckle.

Another approach to improve the echogenicity of devices is set forth in Bosley et al., U.S. Pat. No. 5,201,314. This patent describes a material having an acoustic impedance different from that of the surrounding medium, and improved scattering. The material may be the device itself or a thin interface layer including hard particles such as metal or glass. The presence of spherical indentations formed or embossed on the device surface is said to produce enhanced scattering.

One problem with this approach is that the interface layer is generated during the extrusion process for forming a plastic device, or by soldering, or ion beam deposition, which are inapplicable to many devices, and are expensive and difficult to control. Also the differences in acoustical properties between glass or metal and body cavities are not very large, so echogenicity is not greatly enhanced. Further, the described devices are not smooth since the echogenicity is produced either by indentations in the surface or the addition of metal or glass balls of diameter greater than the thickness of the interface layer. The presence of the particles complicates the manufacturing process, and may weaken the surface of the device which can lead to sloughing of particles, device failure, or instability of the desired effect. Such coatings have not found their way into the market.

SUMMARY OF THE INVENTION

This invention satisfies a long felt need for improving the ultrasound imaging of biomedical devices. The coatings of the invention provide highly echogenic devices which are readily recognized from surrounding tissue or fluid under ultrasound imaging.

The invention succeeds at providing a broadly applicable method of enhancing the ultrasound visibility of surfaces, an objective which previous efforts have failed to reach. The invention solves two problems of the prior art—providing the medical device with an acoustic impedance quite different from that of the animal or human tissue into which it is placed (high acoustic impedance differential), and increasing ultrasound scattering—by a simple, inexpensive, reproducible means of applying a polymer composite coating that has acoustical irregularities. The coatings of the invention are easily made by a variety of methods. They do not require solid particles or particle preparations and do not require machining or extrusion, elements employed in the prior art. Nonetheless, the coatings of the invention provide improved echogenicity.

An adherent, smooth coating employing acoustical irregularities to provide an increased acoustical impedance differential and increased ultrasound scattering differs from prior approaches, and was not previously known or suggested. Such a coating provides advantages that were not previously appreciated, such as broad applicability, the possibility of applying the coating after the device is manufactured, low cost, uniformity, and adaptability to be combined with other coating technologies such as lubricious coatings and coatings containing pharmaceutical agents.

A coated device prepared according to this invention is easily discernable under ultrasound imaging regardless of the angle to the transducer. Since the device is easily recognized against the background tissue or fluid, its exact location is easily identified. This positional certainty can greatly facilitate medical procedures such as biopsies, abscess drainage, chemotherapy placement, etc.

The coatings of the invention include echogenic features, such as discrete gas bubbles and pores, providing acoustically reflective interfaces between phases within or on the coated surface. These interfaces provide an acoustical impedance differential that is large, preferably several orders of magnitude. The shape of the bubbles or other gaseous spaces also improves scattering so that a device may be imaged at virtually any angle.

The advantages and objectives of the invention may be achieved by entrapping gas bubbles in a smooth, thin, biocompatible coating which can be applied to virtually any biomedical device. Gas bubbles are desirable to provide an acoustic impedance mismatch (acoustical impedance differential) much greater than can be obtained by previous inventions. Gas bubbles, especially of small diameter less than about 10 microns, are difficult to stabilize, and satisfactory methods for producing them are a further advantage of this invention. The presence of bubbles entrapped in a thin coating, preferably about 5 to about 50 microns thick, greatly enhances the echogenicity of the device while leaving the device surface very smooth so as to be virtually undetectable by the patient or physician.

According to the invention, a general method for increasing the echogenicity of an object when placed in an ambient material and subjected to ultrasound comprises: providing a coating liquid comprising a film-forming constituent; applying the coating liquid to the object; allowing the film-forming constituent to form a film comprising a solid matrix; and providing the film with an echogenic structure presenting echogenicity-increasing gas/non-gas interfaces when the object is placed in the ambient material. The echogenic features are preferably discrete compressible gaseous spaces enclosed within the film, pores capable of entrapping gas when the object is placed in the ambient material, or combinations.

The method preferably comprises including a reactive material in the coating liquid, and contacting the reactive material with a reactor to produce gas. In a preferred embodiment, the reactive material is a diisocyanate such as toluene diusocyanate or a diisocyanate prepolymer, the reactor is a hydrogen donor selected from the group consisting of liquid water, steam, water vapor, an alcohol, and an amine, and the gas is carbon dioxide. In other embodiments, the reactive material is a carbonate or bicarbonate salt, the reactor is an acid, and the gas is carbon dioxide; the reactive material is a diazo compound, the reactor is ultraviolet light, and the gas is nitrogen; the reactive material is a peroxide compound, the reactor is selected from the group consisting of an acid, a metal, thermal energy, and light, and the gas is oxygen.

The gas may be chlorine, hydrogen chloride or other gas with a vapor pressure higher than air.

In a preferred embodiment, the film-forming constituent is a reactive polymer-forming material, the applying step comprises reacting the reactive polymer-forming material to produce a polymer matrix and gas, and the echogenic features comprise features selected from the group consisting of discrete compressible gaseous spaces enclosed within the film, pores capable of entrapping gas when the object is placed in the ambient material, and combinations.

The method may comprise etching the film by chemical or physical means to produce the echogenic features.

The coating liquid may comprise a compound selected from the group consisting of perfluorocarbons, hydrocarbons, halogenated hydrocarbons, and other materials having a sufficiently high vapor pressure as to generate gas bubbles upon heating of the coating liquid to a predetermined temperature, and further comprising heating the coating liquid or the film to the predetermined temperature to produce gas bubbles.

The gaseous space may be produced by including in the coating a solid compound having a sublimation pressure sufficient to generate bubbles upon heating to a predetermined temperature, and heating the coating liquid or the film to the predetermined temperature to produce gas bubbles.

The coating liquid may be sonicated or otherwise agitated to produce bubbles from about 0.1 to about 300 microns, preferably from about 1 to about 50 microns, most preferably from about 5 to about 10 microns, before applying the coating liquid to the object. Alternatively, one may incorporate pre-formed polymer bubbles of a few microns in diameter within the coating liquid and hence in the polymer matrix. Another option is to include small particles with a diameter of a few microns with micropores on the order of 0.1 micron.

The film-forming component is preferably a dissolved polymer which is cast on a surface and from which the solvent is evaporated; a reactive monomer or pre-polymer reacted to form a polymer; or a thermosetting melted polymer solidifying upon cooling. The coating may involve reacting the polymerizing monomer or pre-polymer to produce a polymer matrix and gas, and trapping the gas in the polymer matrix, and/or allowing it to form micropores on the surface capable of entrapping gas when inserted into the target material. Isocyanate reacted with water to produce polyurethane and carbon dioxide is one example.

Another embodiment involves selecting the coating liquid such that the concentration of solvent is sufficiently high to dissolve the polymer, and the concentration of non-solvent is below the level at which the polymer will precipitate; and after applying the coating liquid, increasing the proportion of non-solvent to cause precipitation of a polymer matrix containing echogenic interfaces. The step of increasing the proportion of non-solvent may be evaporating the solvent, adding a non-solvent, or adding steam.

Before applying the echogenic polymer layer, a pre-coat and/or a base coat may be applied to the object. After the echogenic layer is applied, a top coat layer may be applied to the object without eliminating the increased echogenicity of the coating. If the echogenic layer has cavities, the top coat may reduce the wetability of the echogenic layer so as to promote the entrapment of air in the cavities.

Another aspect of the invention is a coating liquid for producing an echogenic coating on a substrate, comprising a liquid vehicle, a constituent that forms a coating when the coating liquid is applied to the substrate, and a means for providing gas/non-gas interfaces in the coating. The interface-providing means are preferably selected from the group consisting of gas bubbles in the coating liquid, a reactive material that generates gas upon reaction with a reactor, and a combination of components that causes precipitation of solids with entrapped gas during coating. The film-forming component is preferably selected from the group consisting of albumin, carboxylic polymers, cellulose, cellulose derivatives, gelatin, polyacetates, polyacrylics, polyacrylamides, polyamides, polybutyrals, polycarbonates, polyethylenes, polysilanes, polyureas, polyurethanes, polyethers, polyesters, polyoxides, polystyrenes, polysulfides, polysulfones, polysulfonides, polyvinylhalides, pyrrolidones, rubbers, and thermal-setting polymers.

The combination of components that causes precipitation of solids preferably comprises a solvent/non-solvent mixture and an inclusion-former, the concentration of solvent is sufficiently high to dissolve the inclusion-former in the coating liquid, and the concentration of non-solvent is sufficiently high to cause the inclusion-former to precipitate as an inclusion in the coating during evaporation of the solvent from the coating liquid, and to entrap gas.

In a third aspect of the invention, an object comprises a substrate and an echogenic surface or coating comprising a solid matrix and an echogenic structure that presents gas/non-gas interfaces at or near the surface of the object when the object is placed in an ambient medium, the interfaces providing the object with enhanced ultrasound visibility. The gas/non-gas interfaces preferably provide an acoustic impedance mismatch at the surface of the device of at least a factor of about 25.

The interfaces are preferably selected from the group consisting of interfaces between the matrix and discrete compressible gaseous spaces enclosed within the matrix, interfaces between the matrix and gas trapped in pores on the matrix, interfaces between gas trapped in pores on the matrix and the ambient medium, and combinations. The matrix preferably comprises a precipitate formed in the matrix and presenting echogenic gas/matrix interfaces. The echogenic structure preferably comprises gaseous spaces selected from the group consisting of pores, bubbles, channels, and cavities having a dimension selected from diameters or widths between 0.1 micron and about 300 microns, preferably between 1 micron and about 50 microns. More preferably the gaseous spaces are pores with a diameter of about 1 to about 10 microns, channels about 5 to about 50 microns wide and about 20 to about 500 microns long. The echogenic surface preferably consists essentially of the matrix and the gaseous spaces, or may further comprise solid precipitated material.

Preferably less than about 50%, more preferably about 10% to about 20% of the surface area of the object is made up of gaseous spaces. So long as the space holds gas, it appears that the size distribution of the gaseous spaces does not significantly affect the echogenicity of the coating. That is, a surface of many submicron spaces and a surface of a few multimicron sized spaces may be equally echogenic. The key features contributing to echogenicity are the total percentage of surface area made up by gaseous spaces, the compressibility of the spaces if they are enclosed (determined by the polymer, thickness, and diameter of the space), and the ability to entrap air when inserted into an ambient material if the spaces are open (determined by the diameter, shape, and hygroscopic nature of the space).

The gaseous spaces may be located within the echogenic layer or between the echogenic layer and a top layer or the target material. Preferably, the gaseous spaces must be compressible. If they are pores or channels with trapped gas exposed directly to the target material, they are suitably compressible. If the gaseous spaces are enclosed within the polymer matrix or covered by a top coat, the material separating the gaseous space from the target material must be thin enough and flexible enough that the gas remains compressible. A gaseous space separated from the material to be visualized by a hard or thick film is not likely to contribute much echogenicity. Preferably, the flexibility of any covering over the gaseous space is such that it does not significantly reduce the compressibility of the underlaying gas, for example by no more than one order of magnitude. This effect is best achieved if there is no more than several microns of coating material over the gaseous space, such as less than about 5 microns, preferably between about 1 and about 2 microns.

In summary, the echogenic structures included within the polymer matrix according to the invention may be open pores or channels capable of trapping air at the surface of the coating, closed bubbles or channels within the polymer matrix, pores or channels that are thinly covered with a top coat layer, and gas-entrapping intrinsically formed solid or semi-solid inclusions precipitated within the polymer matrix.

The gas/non-gas interfaces are preferably located within the matrix, between the matrix and a top layer, or between the matrix and the ambient material.

The substrate is preferably a medical device such as a catheter, needle, stent, hydrocephalus shunt, draintube, pacemaker, dialysis device, small or temporary joint replacement, urinary sphincter, urinary dilator, long term urinary device, tissue bonding urinary device, penile prosthesis, vascular catheter port, peripherally insertable central venous catheter, long term tunneled central venous catheter, peripheral venous catheter, short term central venous catheter, arterial catheter, PCTA or PTA catheter, and pulmonary artery Swan-Ganz catheter. The coating may further comprise a contrast agent for non-ultrasound imaging such as for x-ray or magnetic resonance imaging.

Further objectives and advantages will become apparent from a consideration of the description and drawings.

BRIEF DESCRIPTION OF THE DRAWINGS

The invention is better understood by reading the following detailed description with reference to the accompanying figures, in which like reference numerals refer to like elements throughout, and in which:

FIG. 1A shows an ultrasound image of a phantom model of blood and liver, with an uncoated wire inserted (not visible). FIG. 1B shows an ultrasound image of a wire with an echogenic coating according to the invention.

FIG. 5 illustrates the enhanced echogenicity of a coated 22 gauge needle in a New Zealand White rabbit kidney as imaged by a Shimadzu SDU-350A ultrasound system with a 7.5 MHz probe. The left column for each rabbit shows the visual rating score for coated needles according to Example 1 and the right column shows the much lower rating for uncoated needles.

FIG. 6A shows an ultrasound image of a breast phantom with a simulated cyst. An uncoated needle is not visible. FIG. 6B shows the corresponding ultrasound image of a needle with an echogenic coating according to the invention.

DETAILED DESCRIPTION OF THE PREFERRED EMBODIMENTS

Figure 1A:
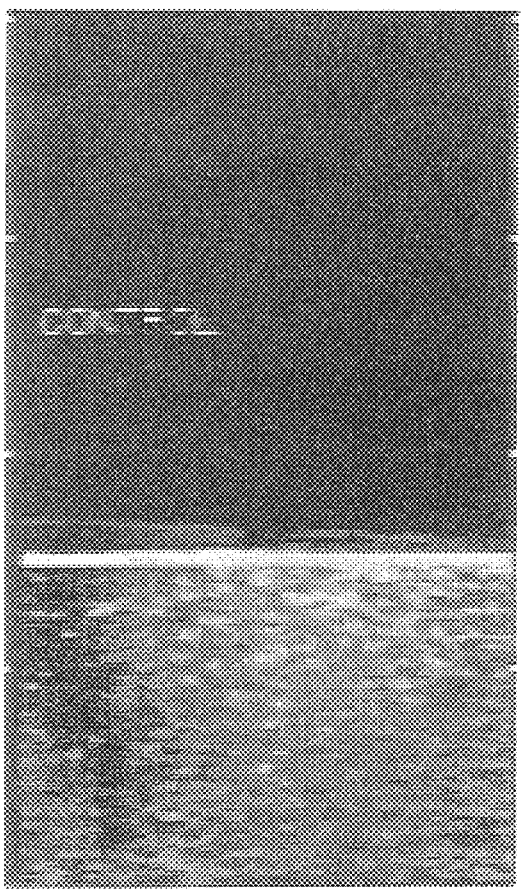
FIGS. 1A and 1B illustrate the enhanced echogenicity of a wire coated according to the invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose. All articles and patents referred to in this application are incorporated herein by reference as if each were individually incorporated by reference.

Echogenicity is the result of backscatter (180 degree reflection back to the transducer) caused by a difference in acoustical impedance. The greater the impedance differential (mismatch), the greater the echogenicity (backscatter).

Acoustic impedance of a material decreases as compressibility increases and as density decreases. Thus, solids have the highest impedance because they are uncompressible and dense. Gases have the lowest impedance because they are compressible and not dense. Liquids fall in between. Solids impede sound beams more than liquids, by up to about one order of magnitude, and liquids impede sound beams better than gases, by several orders of magnitude. Thus, an interface between a solid and a gas produces the highest possible acoustic impedance mismatch, due to differences in compressibility and density. Interfaces between different types of solids, semi-solids, liquids, and gases can also contribute to echogenicity to a lesser but significant degree.

The inherent acoustic impedance of a coating is very difficult to measure. However, the following table demonstrates the vastly different impedance (proportional to the product of density and compressibility) for gases compared with liquids and solids. Small differences from one gas to another or one solid to another makes very little difference on a log scale. However, the orders of magnitude difference between a solid and a gas is easily distinguished on the (log) echogenicity scale. This huge difference in acoustic impedance between a gas and a solid accounts for one aspect of the advantages of the present invention.

TABLE 1

| Material | Compressibility* (cm/dyne) | Density* (g/cc) |
| --- | --- | --- |
| Air | $2.3 \times 10^{-4}$ | $1.29 \times 10^{-3}$ |
| Water | $4.6 \times 10^{-11}$ | 1.00 |
| Erythrocyte | $3.4 \times 10^{-11}$ | 1.09 |
| Aluminum | $1.3 \times 10^{-12}$ | 2.7 |
| Nickel | $5 \times 10^{-13}$ | 8.8 |

Sources: CRC Handbook of Chemistry and Physics, 64th Edition, R. C. Weast, ed. (CRC Press, Inc. Boca Raton, FL 1984); Perry's Chemical Engineer's Handbook, 6th Edition, D. W. Green, ed. (McGraw-Hill 1984); Practical Handbook of Materials Science, C. T. Lynch, ed. (CRC Press, Inc., Boca Raton, FL 1989).

A comparison of impedances for some common materials demonstrates that most materials are at most one order of magnitude different from water (or tissue) except gases (represented by air) which are several orders of magnitude different in impedance.

TABLE 2

| Material | | Characteristic impedance c.g.s. Rayl × $10^{-5}$ (g. cm$^{-2}$ sec$^{-1}$) × $10^{-5}$ |
| --- | --- | --- |
| Non-biological | Air at S.T.P. | 0.0004 |
| | Castor Oil | 1.43 |
| | Water | 1.48 |
| | Polythene | 1.84 |

TABLE 2-continued

| Material | | Characteristic impedance c.g.s. Rayl × $10^{-5}$ (g. cm$^{-2}$ sec$^{-1}$) × $10^{-5}$ |
| --- | --- | --- |
| | Perspex | 3.20 |
| | Aluminium | 18.0 |
| | Mercury | 19.7 |
| | Brass | 38.0 |
| Biological | Aqueous humour of eye | 1.50 |
| | Vitreous humour of eye | 1.52 |
| | Brain | 1.58 |
| | Blood | 1.61 |
| | Kidney | 1.62 |
| | Human tissue, mean value | 1.63 |
| | Spleen | 1.64 |
| | Liver | 1.65 |
| | Muscle | 1.70 |
| | Lens of eye | 1.84 |
| | Skull-bone | 7.80 |
| | Fat | 13.8 |

Source: Table 1.4 from Wells, Physical Principles of Ultrasonic Diagnosis (Academic Press London, 1969)

The acoustic impedance differential (or mismatch) between two objects is given here as a pedance of the object having the higher impedance divided by the impedance of the object having the lower impedance. Coatings according to the invention preferably provide acoustic impedance differentials at echogenic interfaces of at least about a factor of 3, more preferably about a factor of 10, yet more preferably at least about a factor of 25 (the difference between brass and water), most preferably more than about a factor of 100.

An echogenic coating according to the invention is a complex structure that may have one or a combination of several physical forms. It is a coating, a material that forms a thin essentially continuous layer over the substrate, and could be referred to as a film. It may be a complete solid mixture of polymers, and includes intrinsic acoustically reflective echogenic features such as gaseous spaces. The spaces may present some discontinuity in the film without detracting from the adhesion of the film to the substrate.

A film-forming component according to the invention is a polymer or polymer-forming material or similar material that may be dissolved or suspended in a coating liquid, such that when the coating liquid is applied to a substrate, the film-forming component forms a suitable thin layer or film upon evaporation of the solvent or suspending liquid. Many examples are provided. The thin layer or film may be said to comprise a solid matrix of the dried and/or reacted film-forming component. The solid matrix of the film has echogenic features at the surface or within the matrix.

An echogenic feature of a coating according to the invention means a structure that is acoustically reflective in ultrasound applications and thereby increases the visibility of the coating and coated objects. Reflective echogenic features according to the invention may include gas bubbles, irregular gas pockets, cavities, pores, closed gas-containing channels, or microscopically raised and depressed surface regions of the polymer matrix presenting an irregular relief capable of trapping air when inserted into a tissue.

The coating mixture may include additives, and solvent residues blended together. Alternatively, the coating may be a complete solution, defined as a mixture uniformly dispersed throughout the solid phase with homogeneity at the molecular or ionic level, or it may be a combination of dissolved and mixed components, such as a mixture of a polymer coating solution and gas bubbles. The coating may take the form of a composite, defined as a structure composed of a mixture or combination of polymer and gas bubbles. It may be a blend, that is a mixture so combined as to render the components indistinguishable from each other. It may also be referred to as a matrix of polymer in which gas bubbles and other constituents and structures are dispersed. The coating overall may comprise separate layers, discrete or intermingled, each of which may have any or several of these forms.

The term ultrasound is intended to encompass presently known or subsequently developed vibrational signals such as an acoustical signal or beam used to generate a signal based on reflection. Ultrasound technologies available currently generally have resolution larger than that of red blood cells having a diameter of 5 to 10 microns. However, resolution as low as about 0.5 microns may be possible, so gas spaces that small or even as small as 0.01 microns may be desirable according to the invention. Depending on the coating structure, gas spaces as big as 300 microns may be useful to provide enhanced echogenicity. In most cases, however gas spaces with a diameter of greater than 1 micron, preferably about 5 to about 10 microns, up to about 20 microns, are satisfactory. These are suitable in coatings with an average thickness of about 10 to 50 microns. Larger spaces may be appropriate in thicker coatings up to several hundred microns thick.

Figure 2:
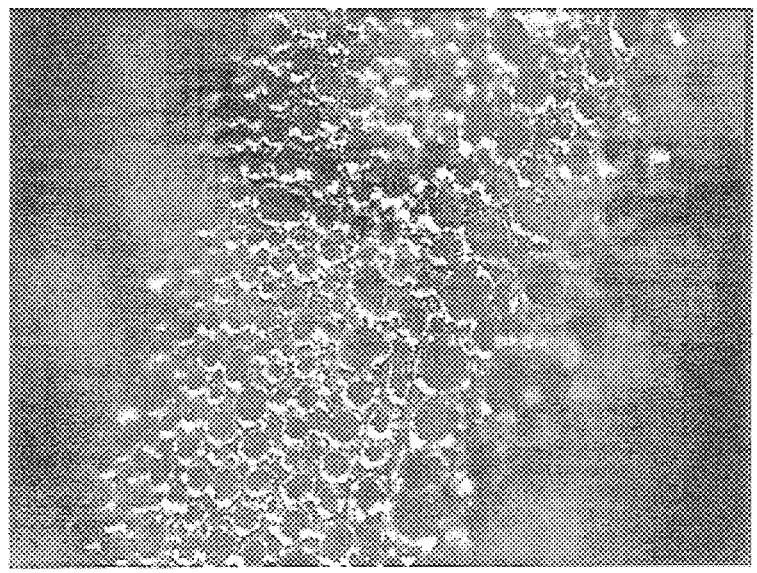
FIG. 2 is a light microscopic image (100×) showing a needle with an echogenic coating formed from isocyanate.
Figure 3:
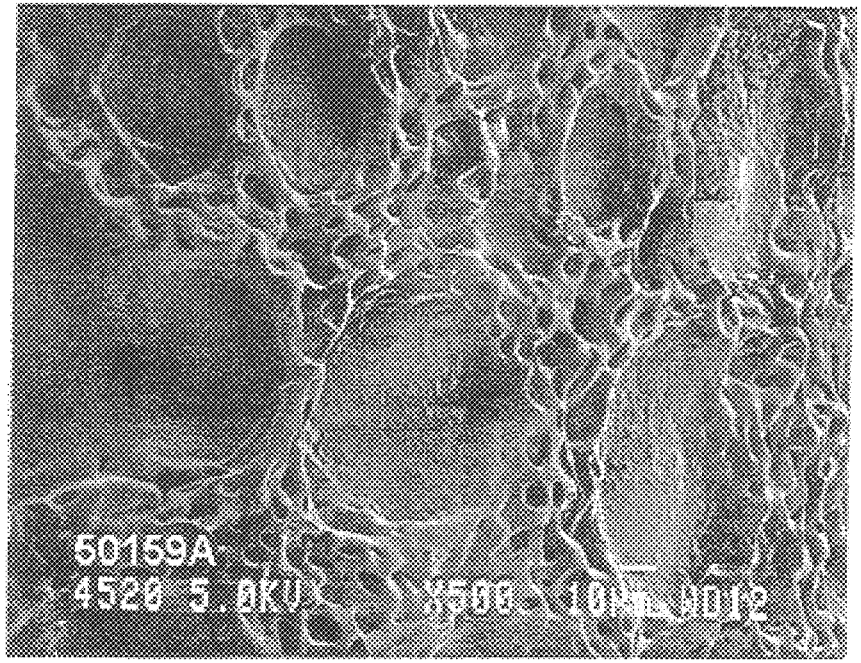
FIG. 3 is an electron micrograph at 500× magnification showing the same type of coating as in FIG. 2, with 30 to 70 micron cavities and 1 to 10 micron pores.

Increased echogenicity according to the invention may be due to bubbles or small craters of these general sizes, preferably about 1 to 10 micron diameter. The microscopic appearance of these coatings, showing the bubbles and craters, is shown in FIGS. 2 and 3. In a thin coating, despite such craters, the coating still feels smooth. In a thick coating, with higher relief, the surface may become rough, so conditions should preferably be controlled to minimize surface relief so as to produce a smooth coating for medical applications. For example, drying a viscous bubble-containing polymer solution at high temperature may lead to a rough coating. On a macroscopic scale the coating should remain smooth for medical devices to avoid discomfort to the patient and misinterpretation by a physician when attempting to place the device in a target site.

As used here, smooth means sufficiently smooth so as not to cause difficulty in inserting a coated object into a target material, which may be determined by a person of ordinary skill. A reasonable predictor of smoothness in use is to rub a finger along the surface of the coating and determine whether it feels smooth or rough. Smoothness to the touch is generally adequate according to the invention.

When an echogenic surface having small irregularly shaped craters or pores is submerged in an aqueous (body) fluid, surface tension prevents these small craters from being filled in by water and air may be entrapped on the surface of the device. Although larger and rounder or more regular cavities may be present as well, they are more likely to fill with water leaving a lower level acoustic impedance differential. This feature applies when the coating is placed in solid or semisolid tissue or material, forming a gas/liquid interface if physiological fluid contacts the coating, a semisolid/gas interface if a gel material (such as coupling gel) contacts the coating, or a solid/gas interface if solid material contacts the coating. The echogenic features are stable under conditions of use such as soaking, rubbing, pressure changes, and agitation. The coating provides enhanced echogenicity in each of these situations.

Thus, in one embodiment of the invention, to take advantage of acoustic impedance differential, gas bubbles are entrapped in a smooth thin coating which can be applied to virtually any biomedical device. Gas bubbles are desirable to provide an acoustic impedance mismatch much greater than could previously be obtained. Generally, in such an embodiment, craters and pores are formed at the surface of the coating, and contribute to the echogenicity of the coating.

Another embodiment of the invention comprises channels in discontinuous matrices in a coating, which also provides a desirable acoustical impedance mismatch and improved echogenicity according to the invention. An irregularly shaped channel is desirable as it may trap air in pockets and may also have interfaces between materials having mismatched acoustic impedance to provide echogenicity. The size of the channels should be in the same general range as with bubbles and cavities, and should not be so great as to cause discontinuities in the coating such that the coating would peel off. Thus, a continuous air channel or layer would not be desirable according to the invention.

The polymer components of the coating may be precipitated together in such a way as to generate intrinsic acoustically reflective interfaces, such as solid/gas interfaces. This approach is advantageous in that no extraneous solids need to be added to the coating to provide the acoustically reflective interfaces.

The echogenic coating liquid formulations of the invention comprise an organic solvent and a polymer system adapted to produce acoustically visible structures when coated on a substrate. The polymer system may be a polymer and bubbles having a diameter between about 1 micron and about 50 microns; a reactive polymerizing monomer that generates gas during polymerization; or a polymer solvent/non-solvent mixture wherein the concentration of solvent is sufficiently high to dissolve the polymer in the coating liquid, and the concentration of non-solvent is sufficiently high to cause the polymer to precipitate during evaporation of the organic solvent from the coating liquid entrapping gaseous bubbles with the precipitate. Such a coating liquid may be a complete solution, meaning a mixture uniformily dispersed throughout the liquid phase with homogeneity at the molecular or ionic level, or it may be a mixture of a polymer solution and a gas phase, and possibly gas containing particles dispersed as a suspension.

Echogenic coatings can be prepared using a wide variety of polymers. Bubble trapping polymers include cellulose esters, polyurethanes, albumin, other proteins, polyvinyl pyrrolidones and others that are known to those skilled in the art to be capable of trapping small bubbles. Generally a viscous preparation is preferred. Preformed bubbles such as gas entrapped in albumin microspheres (for example Albunex® spheres, Molecular Biosystems, Inc.) may be used. Polymer-forming materials that generate gas include isocyanate prepolymers and diazo compounds. Preferred materials are isocyanates and albumin.

The following gas-producing compounds could be used in the practice of this invention: polyisocyanates, such as polymethylene polyphenylisocyanate, 4, 4-diphenylmethane diisocyanate, and 2,4-toluene diisocyanate, sodium carbonate, sodium bicarbonate, aromatic diazonium salt stabilized compounds, prepolymers or other addition compounds such as oligomers or cooligomers of isocyanates wherein the isocyanate is selected from toluene diisocyanate, hexamethylene diisocyanate, cyclohexane diisocyanate, isophorone diisocyanate, 4, 4' diphenylmethane diisocyanate, or a prepolymer, such as trimerized hexamethylene diisocyanate biuret. Such prepolymers are available under trade names such as: Desmodur (Bayer AG), Tycel (Lord), Hypol (Hampshire), Andur (Anderson Developer Company), Papi and Voranate (Dow Chemical Company).

The isocyanate component of the coating liquid is preferably in a concentration of between about 20% and about 40%, and the solvent system for it preferably comprises about 15 to about 48% dimethylsulfoxide, up to about 35% tetrahydrofuran, up to about 30% toluene, up to about 32% cyclohexanone, and suitable amounts of hexane, 2-butanone, xylene, ethyl acetate, dichloromethane, 1,1,1-trichloromethane, n-methylpyrrolidone, and n-butyl acetate.

Solvents for the echogenic coating layer include ketones, esters, aromatics, lactones, amides, halogenated hydrocarbons, alcohols, amines and other common solvents. Any solvent system that is capable of dissolving all constituents of the coating into a homogeneous solution may be selected. Preferred solvents are tetrahydrofuran, dimethylsulfoxide, and acetone. For precipitated coatings, preferred nonsolvents include ethanol, isopropanol and water.

In most cases, air and gases such as carbon dioxide and nitrogen generated in situ are adequate to effect echogenicity enhancement and offer low cost and simplicity of manufacture. Any gas could be used, and further echogenicity enhancement might be obtained using gases which are more highly compressible, less dense, and are less likely to dissipate when drying the coating and are less soluble or slower diffusing in physiological solutions.

Substrates to which echogenic coatings according to the invention may be applied include metals such as stainless steel, nickel, gold, chrome, nickel titanium alloy, platinum and others; plastics such as silicone, polyurethane, polyethylene, polyamide, polyvinylchloride, latex and others; drug particles; and capsules. Preferred devices include needles, guidewires, catheters, surgical instruments, equipment for endoscopy, wires, stents, angioplasty balloons, wound drains, arteriovenous shunts, gastroenteric tubes, urethral inserts, laparoscopic equipment, pellets, or implants.

Echogenic coatings according to the invention may be applied to a device as one or more layers. In a simple embodiment, a matrix polymer is dissolved in an organic solvent and aerated to produce a coating liquid having bubbles of the desired size. The coating liquid is applied to the substrate, and dried rapidly enough to set the bubbles in place, to provide an echogenic coating. However, substrates such as metal guidewires, stainless steel needles, and silicone, polyethylene, and nylon catheters, and other polyolefin and polyamide substrates may not allow for adequate adhesion of the echogenic layer.

In a multilayer embodiment, the surface is first treated to enable strong adhesion of the echogenic coating to the device. This treatment may include applying a first layer, or pre-coat. and a second layer, or base coat, if necessary, to effect adhesion of the echogenic coat to the surface. The active echogenic layer containing echogenic interfaces is then applied over the dried base coat to enhance the echogenicity of the device. Optionally, a fourth layer, a finish or top coat, may be applied to improve the durability of the echogenic coating against abrasive forces, to enhance lubricity, provide a smoother surface, to protect the echocoat from deleterious effects of exposure to body fluids, or to incorporate pharmaceutical agents such as antithrombogenics, antibiotics, and antimicrobials, or to impart other desirable properties, according to methods known in the art. For example, lubricious coatings are described in U.S. Pat. No. 5,331,027, and coatings comprising pharmaceutical agents are described in U.S. Pat. No. 5,525,348. A top coat may also be used to reduce the wetting of the echogenic coating layer. Wetting of the echogenic layer should be avoided as echogenicity may decrease if this echogenic coating swells excessively and releases the otherwise entrapped gas. Additionally, wetting may cause gas entrapped in surface pores or cavities to be released. Enhanced mechanical stability can be useful for applications in which the device may be subjected to high shear forces as may occur if a coated device is forced to move against a bone.

Pre-treatment of the substrate surface may not be required on a substrate if the adhesion between the device surface and the echogenic layer is adequate. Alternatively, a single sub-layer rather than a pre-coat and base coat may be adequate depending on the degree of adhesion between the coating and the device.

In a pre-coat, useful polymers include acrylics, acrylic copolymers, polyolefin copolymers, polyethylene/polyacrylic acid copolymer, chlorinated polyolefin polyacetals, epoxies, mixtures and others known to one skilled in the art. Adhesion on polyolefin surfaces is improved by using polyolefin acrylic copolymers, and adhesion on silicone polymers is improved by using precoat layers which contain polydimethylsiloxane polymers.

In a base coat, typical polymers include polyurethanes, cellulose esters, acrylics, acrylic copolymers, polyacetals, epoxies, others, and mixtures of the above. An example of a basecoat includes cellulose ester, an acrylic polymer, a polyurethane, and 2-hydroxy-4-methoxy benzophenone dissolved in a mixture of solvents including tetrahydrofuran, cyclohexanone, and ethyl acetate.

In a top coat, preferred polymers are hydrophobic polymers such as polyvinylbutyral, polyacetals, acrylics, acrylic copolymers, vinyls and others known to one skilled in the art. Also, one or more top coat(s) also may be applied to further improve the surface smoothness of the coated device. Polymeric solutions of the appropriate viscosity will flow into crevices which may have developed during drying of the echogenic coating and produce a very smooth outer surface in the process. Such top coat compositions can include hydrophobic polymers or hybrid polymers such as polyvinylacetate, cellulose esters, vinylacetal polymers, acrylates, polyurethanes, epoxies, and others. Although the crevices may be filled, there may still be solid/gas interfaces sufficient to improve the ultrasound visibility of the coated device.

In general, the layers of an echogenic coating may be applied as polymers dissolved in a solvent by dipping, spraying or other methods known to those skilled in the art. Other compositions will occur to those skilled in the art to improve adhesion on these or other substrates as needed.

The echogenic coating may be referred to as the ultrasonically active layer and contains interfaces between different materials, such as between a solid polymer phase and a gas (air, carbon dioxide, water vapor, an inert gas, or otherwise). Alternatively, the active layer contains echogenic interfaces between different portions of the coating, such as with the interface between a solid and a gas internally within the coating layer, or at the exterior surface of the product. In general, the most important portion of the coating for echogenicity is at or near the surface, and features well beneath the surface are less important. Hence, the active echogenic layer coat composition is preferably designed to efficiently entrap gas bubbles or matrices containing gas bubbles.

In one embodiment of the invention, advantages may be found in using polymer coatings containing various materials in addition to gas (such as solids, suspensions, and liquids). Differences in echogenic responses are known to exist between various materials, such as different portions of the coating having a different blend of polymer and additives, or shapes such as folds, flaps, or contours of the polymer surface, but most strongly between gases and solids or gases and liquids. Surface irregularities, which can be completely bound within a coating or on the exterior surface, can further enhance the differences in echogenic response, and improve scattering. Thus, in certain embodiments, this invention incorporates microscopic surface irregularities and/or different materials in coatings for application to materials, to achieve enhanced echogenicity.

In another embodiment, echogenic active coating layers may consist of one or more polymer or mixed (hybrid) polymer layers which are applied to a substrate or pre-coated substrate as a coating liquid comprising the polymers in a solvent system. The polymer layer, once applied, may then be exposed directly to a non-solvent liquid for the polymer thereby causing the polymer component to precipitate. This can be done by using a mixed solvent system comprising a solvent for the polymer, and a liquid that is a non-solvent for the polymer. In such cases, the non-solvent liquid may be selected so that it evaporates more slowly than the polymer solvent component. Thus, the solvent system changes from one which can dissolve the polymer to a mixture which is sufficiently rich in the non-solvent component so that the polymer component precipitates onto the substrate. Selected polymers precipitated in this fashion have desirable features such as the ability to trap air or gas during the precipitation process or otherwise provide an echogenically active layer.

Such precipitated layers may also be created by casting the polymer layer to precipitate. For instance, a water insoluble polymer, dissolved in an organic solvent, may be cast on a surface and, while still wet with solvent, be immersed in water or exposed to water vapor such as steam to precipitate the polymer layer, or other treatment that leads to precipitation of the polymer from solution entrapping gaseous spaces in an irregular fashion. The irregularity distinguishes this type of coating from the typical type of polymer coating which is a continuous dried, cured film formed by evaporation of the solvent from a polymer/solvent solution, and is transparent and clear. In this embodiment, the curing process is interrupted by an aqueous precipitation step that causes the polymer component to form a solid having a different, irregular structure, one that is white, and reflects light in all directions. The gas entrapping irregularities due to precipitating the polymer coating during formation provide an enhanced echogenic response.

In a third embodiment, it is possible to incorporate polymer components which are capable of producing gas vapor bubbles upon treatment. Such bubbles can then be trapped in the polymer layer. It is also possible to create bubbles in the liquid polymer solution before casting the layer. The resulting layers are found to have echogenic responses which are significantly different than typical body tissues such that objects coated with them are rendered more readily apparent against typical body tissues.

One example comprises:

a) providing an echogenic coating solution including an isocyanate polymer in an organic solvent;

b) applying the echogenic coating solution to a device by dipping or spraying;

c) drying the device coated with the echogenic coating solution for a few minutes at room temperature to remove some of the organic solvent;

d) exposing the coated device to water to generate bubbles in situ; and e) drying the coated device to remove the remaining solvent.

The reaction of the isocyanate is:

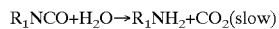

$R_1NCO + H_2O \rightarrow R_1NH_2 + CO_2 \text{(slow)}$

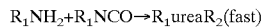

$R_1NH_2 + R_1NCO \rightarrow R_1ureaR_2 \text{(fast)}$

This method is distinct from prior art methods of using isocyanate to form a hydrogel as in Lambert, U.S. Pat. No. 4,585,666. Here, reaction conditions are adjusted to maximize generation of gas and entrapment of bubbles within the solid matrix of the coating film. For example, the reaction is performed at or near room temperature to prevent gas from escaping too quickly. In the Lambert method, the reaction is typically run at an elevated temperature and with hydrophilic components such as polyvinylpyrrolidone such that gas is not entrapped. Thus, an aspect of the invention is to react the reactive component under temperature and humidity conditions that generate and entrap echogenic quantities of gas within the coating film, and without components that would interfere in such a process.

A diazonium salt reacted with ultraviolet light to produce nitrogen is another example of this approach. An acid base reaction such as with bicarbonate of soda may be used. Other ways to generate gas in situ will be evident to a person of ordinary skill.

Another embodiment comprises preparing a viscous composition, of e.g. acrylic latex polymer, polyvinylpyrrolidone, albumin or other polymer; sonicating with enough energy to produce a coating liquid containing bubbles of 5 to 20 micron diameter; immediately coating the device with this echogenic coating solution by dipping or other means known to one skilled-in-the-art; then drying at, for example, about 80° C. or less to harden the coating without destabilizing the bubbles. For a given mixture, the time and parameters for sonication may readily be determined empirically, e.g. by observing samples under a microscope, and once suitable conditions are determined, these may be used repeatedly and reproducibly. Other means may be used to generate bubbles, too, such as shaking, mixing, blending, and so forth, so long as the desired bubble size is achieved.

Figure 4:
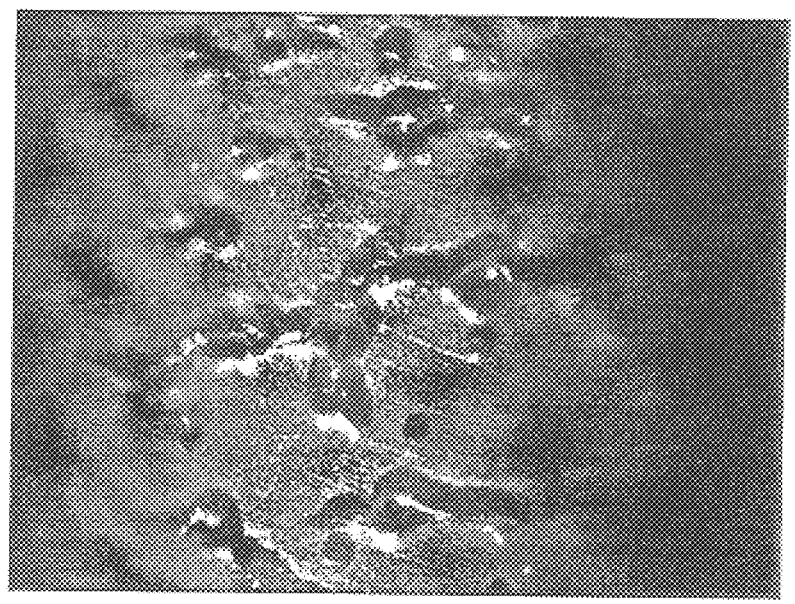
FIG. 4 is a light microscopic image (100×) of a needle with a channel coating formed from a sonicated albumin solution.

Yet another embodiment is to prepare a bubble-containing echogenic coating solution as in the preceding paragraph, and apply it to a substrate. The coated device is then dried slowly at room temperature or even colder. As a result of the low temperature drying, bubbles escape and collapse, and the dried coating appears to consist of a matrix of channels of 5 to 20 microns width and varying length. Such a coating is shown in FIG. 4. These channels may contain trapped air, and so enhance the echogenicity of the device. Also, the irregular shape of the coating may contribute to increased acoustic impedance differential and increased scattering.

A different embodiment involves selective extraction. The method involves forming a layer of two components, a matrix component having a relatively lower solubility in an extraction solvent, and an extractable component with a relatively higher solubility in the extraction solvent. The matrix component must have good adhesion to the substrate after being deposited. Preferably the matrix component is nitrocellulose, the extractable components are camphor and dibutylphthalate, and the extraction solvent is isopropanol.

After forming the film, the extractable component is selectively extracted in the extraction solvent, leaving the matrix component behind as a solid matrix film containing voids. Upon drying, such a layer is echogenic. Similar results may be achieved by chemical or physical etching of a coating surface.

Figure 1B:
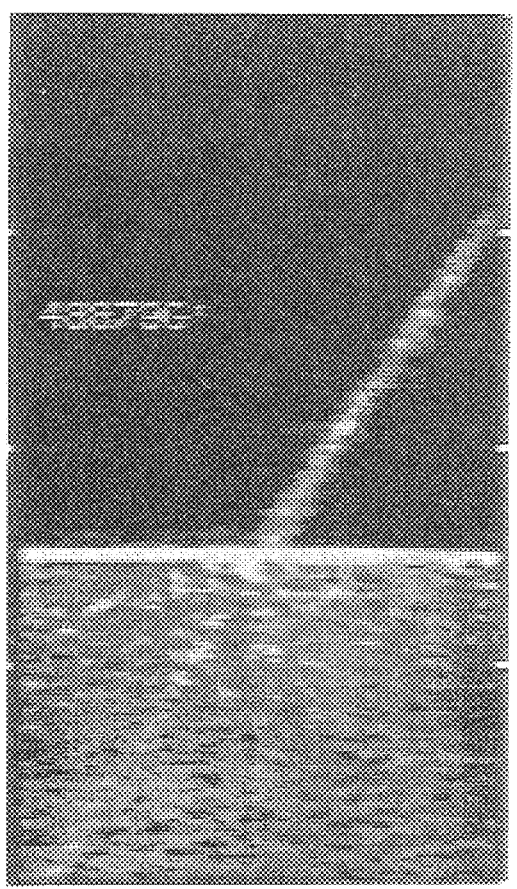

Echogenicity can be measured by imaging a device against a suitable background—water, tissue—and subjectively evaluating image optical densities. FIGS. 1A and 1B show the enhanced echogenicity of a coated wire according to the invention using a water-immersed "phantom" which simulates the echogenicity of various tissues and is designed for reproducible placement of the coated device being tested. The images are qualitatively reproducible.

To use this phantom, a sample (such as a needle, wire, catheter) is inserted into a 2 mm diameter hole drilled into the phantom and off-axis from the ultrasound beam. An image is produced using an ultrasound transducer focused on the control material in the phantom.

As evidenced by FIG. 1A, an uncoated wire is not visible at all as sound waves are reflected away from the transducer. The bright area on the bottom half of the image is a plastic composite material which simulates the echogenic characteristics of liver tissue. The darker area on the top of the image is water, which has an echogenicity similar to that of blood. The wire is inserted diagonally into a hole drilled in the phantom.

FIG. 1B shows a wire coated with an isocyanate-based coating according to the invention in the same phantom. The wire coated according to the invention is plainly visible against the water phase, and it is plainly visible against the phantom. This type of coating had the best visibility among those tested. These results indicate that the coating would be visible in blood and in tissue of similar ultrasound qualities to liver. The uncoated wire, FIG. 1A, is completely invisible under these imaging conditions.

Figure 6A:
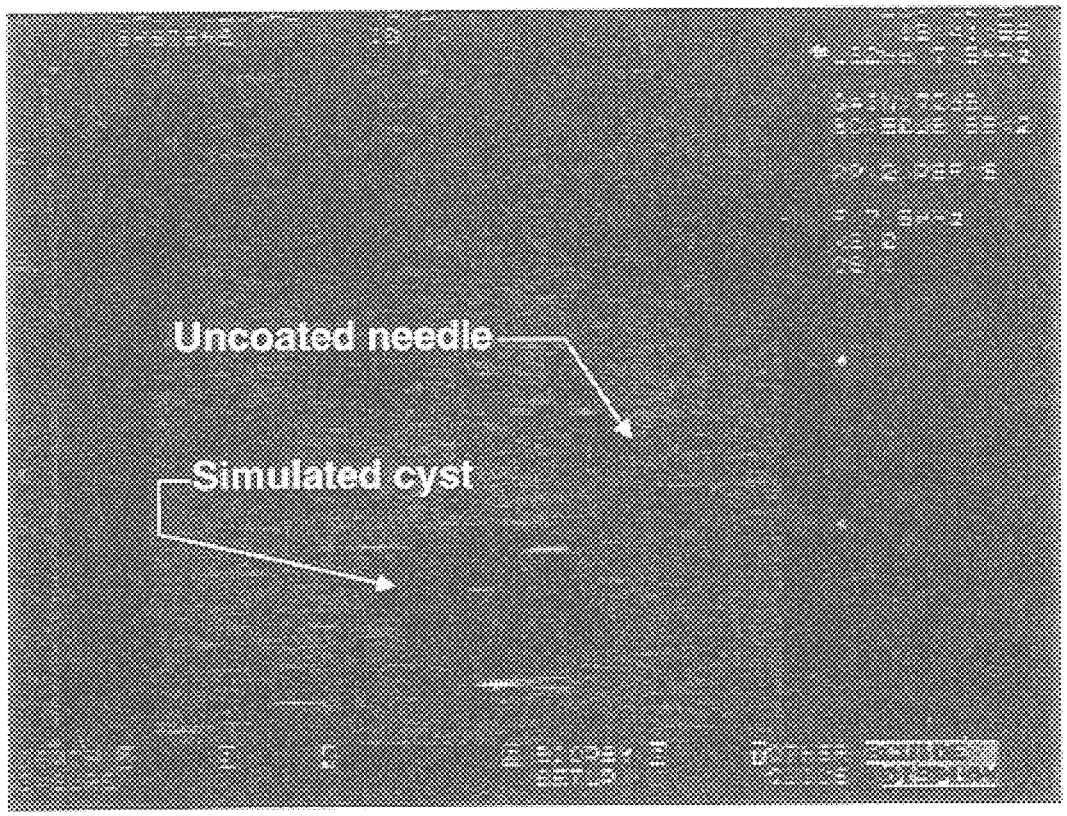
FIGS. 6A and 6B further illustrate the enhanced echogenicity of a 22 gauge needle coated according to the invention.
Figure 6B:
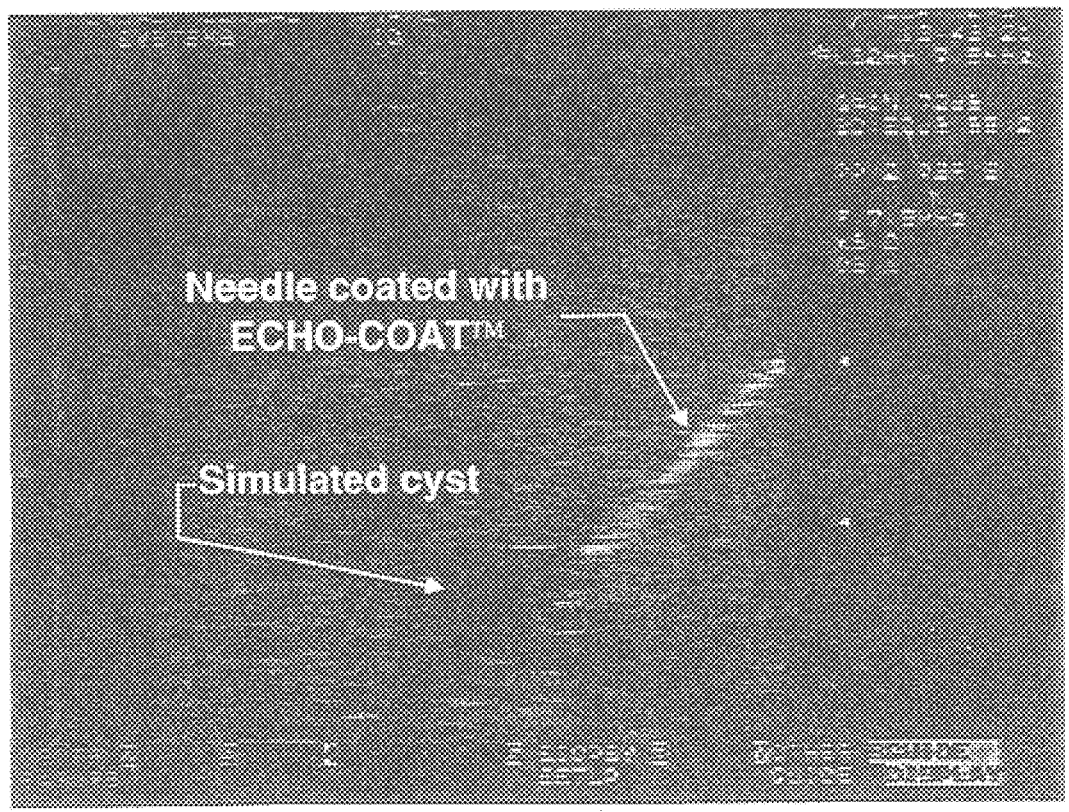

These results were confirmed by imaging in a breast phantom and rabbit kidneys. As shown in FIG. 6A, an uncoated 22 gauge needle is virtually invisible in a breast phantom having a simulated cyst (see "uncoated needle" and "Simulated cyst"), while a similar needle coated as in example 1 is readily visualized under identical conditions (see "Needle coated with ECHO-COAT™"). These results were further confirmed when uncoated and coated needles were imaged in rabbit kidneys. See FIG. 5. FIG. 5 shows the average ratings of three independent observers of five needles per group, one kidney imaged in each rabbit. Only the tip of the uncoated needle may be discerned while almost the entire shaft of the coated needle is visible as well as the tip.

Imaging was done with a Quantum Quad 2000 imaging system at 7.5 MHz, or a Shimadzu SDU-350A system with a 7.5 MHz 150 degree convex probe, although other devices, lower frequencies, and other settings may be used.

The microscopic appearance of gaseous coatings according to the invention is shown in FIG. 2, a light micrograph at a magnification of 100×, and FIG. 3, an electron micrograph at 500× magnification. The coatings had a thickness of about 5 to about 20 microns. The coating has prominent crater-like cavities about 30 to 70 microns in diameter at the surface. The cavities are not very deep, and the coating feels very smooth.

Electron microscopy reveals that this coating also contains a large number of smaller (1 to 10 micron diameter) cavities and/or bubbles as shown in FIG. 3. Without intending to limit the scope of the invention, it is believed that these smaller gaseous spaces contribute more to the increased echogenicity since surface tension may preclude their being filled by water when the device is inserted into a body fluid, whereas the larger cavities are more easily wetted and filled. With an embodiment of the invention having channels as in FIG. 4, ultrasound imaging with a phantom as described above shows an improvement over the signal of an uncoated wire as in FIG. 1A. This improvement is not as great as with the coatings formed with isocyanate. The microscopic appearance of coatings according to this second embodiment reveals long irregular grooves estimated to be about 30 microns wide and 100 to 300 microns long. These grooves apparently are not deep since the coatings feel quite smooth. Such coatings can be made by sonicating an albumin solution, coating, and drying at room temperature.

A precipitated coating also provides an ultrasound image that is an improvement over the uncoated wire shown in FIG. 1A. The microscopic appearance of a precipitate coating appears to be quite smooth, but surprisingly provides improved echogenicity.

Coatings according to the invention are biocompatible, thin, smooth, and adhere strongly to substrates. They are stable in that they retain echogenicity for an extended period suitable for medical procedures, preferably at least one minute, more preferably at least five minutes, most preferably at least an hour. Preferably, they may be used repeatedly over two or more hours without substantial loss of echogenicity.

Such coatings improve the safety and efficacy of numerous procedures. For example, physicians can accurately place coated cardiovascular stents and monitor any migration by ultrasound imaging. Coated biopsy needles are easier to place accurately in a lesion, improving the diagnostic value of the samples obtained. Amniocentesis can be conducted more safely by visualizing the sample needle as well as the fetus. Cutting devices may be accurately placed under ultrasound guidance to improve Laparoscopic surgical procedures. The invention also has application in non-medical fields as will be apparent to those of ordinary skill familiar with the use of ultrasound.

The following examples are offered to illustrate the practice of this invention but are not intended to be limiting.

EXAMPLE 1

A steel wire was dip-coated in a precoat solution consisting of an acrylic polymer, a polyolefin/acrylic co-polymer, and isocyanate, dissolved in a mixture of tetrahydrofuran and cyclohexanone, and cured. The wire was then dip coated in a base coat solution consisting of cellulose ester, an acrylic polymer, and a polyurethane resin, dissolved in a mixture of solvents including cyclohexanone, tetrahydrofuran, ethyl acetate, and benzyl alcohol, and cured. This device was then coated with an echogenic coating solution comprising 20% isocyanate pre-polymer dissolved in a mixture of 50 percent (w/w) dimethylsulfoxide in tetrahydrofuran. The coating was then partially dried at room temperature for 3 to 5 minutes to allow some of the TMF (which is the more volatile solvent) to evaporate. The isocyanate pre-polymer polymerizes on exposure to water and gives off carbon dioxide. The device was dipped in water at room temperature for three minutes to cause the polymerization reaction to occur quickly, trapping bubbles of carbon dioxide and forming pores and craters ranging from about 1 to about 70 microns diameter in the coating. The coating was then dried. Echogenicity increased as compared to uncoated steel wire, as shown in FIGS. 1A and 1B.

EXAMPLE 2

A steel wire was coated with a precoat and basecoat as in Example 1. The wire was then coated with a 20% isocyanate prepolymer dissolved in tetrahydrofuran with 1% surfactant (silicone). Polymerization was brought about by applying steam to the coated device for two minutes. An echogenic coating of the bubble/cavity/pore type was formed.

EXAMPLE 3

An echogenic coating solution contained 90% acrylic polymer in water. This liquid was sonicated for 40 seconds to provide the desired bubble size. A wire was coated with the coating liquid and dried in air at room temperature. An echogenic coating with channels was formed.

EXAMPLE 4

A wire was given a precoat as in Example 1. The coating of Example 3 was applied. An echogenic coating with channels was formed.

EXAMPLE 5

A steel wire was coated first with a precoat and basecoat as in Example 1. This device was then coated with an echogenic coating solution containing 7.8% cellulose acetate butyrate combined with 8% of a polyvinyl pyrrolidone/vinyl acetate copolymer in a solvent mixture of acetone, isopropanol, and 3.4 percent (w/w) water. The coating solution was allowed to dry at room temperature, and a precipitate formed. The coated device showed an increase in echogenicity when compared to a similar uncoated wire.

EXAMPLE 6

A device was dipcoated in an ethanolic solution of 5 percent polyvinylpyrrolidone/vinyl acetate copolymer and dried for 20 minutes at 80° C. An echogenic coating solution consisting of 25 percent serum albumin was prepared and sonicated at high intensity for 20–30 seconds for a four milliliter volume. The pre-coated device then was coated with this echogenic coating and dried for 20 minutes at 80° C. The device was finally coated with a topcoat consisting of 10 percent polyvinyl butyral which was dried for 20 minutes at 80° C. Coated devices demonstrated 10 to 25 times increased echogenicity compared to the corresponding uncoated device.

EXAMPLE 7

A device was pre-coated as in example 1. Then, a 2 percent solution, w/v, of tridodecylmethylammonium heparinate in toluene was diluted 1 part to 3 parts of ethanolic 10 percent polyvinyl butyral, and mixed by vortex mixer to introduce air and form bubbles stabilized by the polymer. The pre-coated device was immediately coated with this solution and dried for 20 minutes at 80° C. Echogenicities approximately double those of the uncoated device were observed.

EXAMPLE 8

Devices were pre-coated as in example 1, then coated with a 45 percent aqueous dispersion of acrylic polymers, sonicated at high intensity for 12 seconds per milliliter of echogenic coating solution, and dried for 20 minutes at room temperature. Echogenicities of these coated devices were 6 to 7 times greater than the uncoated devices.

EXAMPLE 9

A steel wire was given a precoat and a basecoat as in Example 1. 20 percent isocyanate prepolymer was dissolved in a mixture of 49.5 percent tetrahydrofuran, 49.5 percent DMSO, 1 percent water. The device was coated and allowed to air dry at room temperature. A coating was formed which contained bubbles and cavities in the size range of 30–70 microns.

EXAMPLE 10

The coating material and steps were the same as in Example 1. The wire was tested for echogenicity, soaked in water for 60 minutes and retested. The echogenic coating retained its echogenicity, demonstrating the stability of the echogenic coating during an extended period.

EXAMPLE 11

A polyethylene substrate was coated first with a precoat consisting of acrylic and cellulose polymers and then coated with an echogenic coating solution comprising 20% isocyanate pre-polymer dissolved in a 50:50 mixture of dimethylsulfoxide and tetrahydrofuran. The coating was then partially dried at room temperature for 3 to 5 minutes and then dipped in water at room temperature for 3–5 minutes to cause the polymerization reaction to occur rapidly. An echogenic coating was formed.

EXAMPLE 12

A polyamide substrate was coated with an echogenic coating solution comprising 20% isocyanate pre-polymer dissolved in a 50:50 mixture of dimethylsulfoxide and tetrahydrofuran. The coating was then partially dried at room temperature for 3 to 5 minutes and then dipped in water at room temperature for 3–5 minutes to cause the polymerization reaction to occur rapidly. An echogenic coating was formed.

EXAMPLE 13

A polyurethane substrate was coated as in Example 12, also forming an echogenic coating.

EXAMPLE 14

A wire was coated as in Example 1, and then was coated with a top coat solution of polyvinylbutyral in ethanol. The wire was echogenic even though the echogenic coating was covered by another coating layer.

EXAMPLE 15

A wire coated with a precoat and base coat as in Example 1 was then coated with a solution containing 20 percent isocyanate prepolymer dissolved in a 48 percent dimethyl sulfoxide, 32 percent tetrahydrofuran solvent mixture. The coated wire was exposed to water at room temperature for 10 minutes and then dried for 15 minutes at 85° C. The coated wire was tested for echogenicity initially and after 10 and 30 minutes in the liver phantom. The coating maintained its echogenicity over the 30 minute test period.

EXAMPLE 16

A wire was coated as in Example 15, and then was coated with a top coat of 3 percent polyvinyl butyral in ethanol. The coated wire was tested for echogenicity in the liver phantom as in Example 15. A smooth echogenic coating was formed which maintained its echogenicity over the 30 minute test period.

EXAMPLE 17

A wire was coated as in Example 15 and then was coated with a top coat containing polyvinylpyrrolidone (K-90) and cellulose ester in a solvent mixture of ethanol and 4-butyrolactone.

A smooth echogenic coating was formed that was also slippery when wet with water.

EXAMPLE 18

A wire was coated with precoat and base coat as in Example 1. It was then coated with a solution containing 40 percent isocyanate prepolymer in a 50:50 solvent mixture of dimethylsulfoxide and tetrahydrofuran. The coated wire was exposed to water at room temperature for 10 minutes and then dried for 15 minutes at 85° C. An echogenic coating was formed.

EXAMPLE 19

A wire was coated with precoat and base coat as in Example 1. It was then coated with a solution containing 20 percent isocyanate prepolymer and 2 percent silicone surfactant in a mixture of dimethylsulfoxide and tetrahydrofuran. An echogenic coating was formed.

EXAMPLE 20

A wire was coated with a precoat containing a polyolefin/acrylic copolymer and an epoxy resin in a solvent mixture of tetrahydrofuran and cyclohexanone. The wire was then coated with a solution containing 20 percent isocyanate prepolymer dissolved in a 48 percent dimethyl sulfoxide, 32 percent tetrahydrofuran solvent mixture. The coated wire was exposed to water at room temperature for 10 minutes and then dried for 15 minutes at 85° C. An echogenic coating was formed.

EXAMPLE 21

Stainless steel 22 gauge needles were coated with a precoat, a base coat and an echogenic coating as described in Example 15, and inserted into the kidneys of New Zealand white rabbits and imaged with a Shimadzu SDU-350A ultrasound imaging system using a 150° convex probe at 7.5 MHz. Five needles were coated, five were not. Each needle was inserted through ultrasound coupling gel, into the rabbits' skin and into each of the four kidneys of two rabbits. The echogenic coated needles had enhanced visibility in the rabbit kidneys when compared to uncoated needles, as seen in FIG. 5. Even after use in all four kidneys, and being coated with coupling gel for about two hours, the echogenic coated needles retained almost all their enhanced echogenicity.

EXAMPLE 22

A glass slide was coated with a composition containing ethylene acrylic copolymer and epoxy resin in tetrahydrofuran and cyclohexanone, and dried at 85° C. for 30 minutes. Next, the coated glass slide was overcoated with a composition containing nitrocellulose, camphor and dibutylphthalate in tetrahydrofuran, toluene, butyl acetate, ethyl acetate and ethanol, and dried for 30 minutes at 85° C. Next, the coated glass slide was soaked in isopropanol for 10 minutes to extract camphor and dibutylphthalate which are alcohol soluble and leave behind a porous matrix film of nitrocellulose which is not soluble in isopropanol. The sample was echogenic.

EXAMPLE 23

Polyurethane tubing was coated with a solution containing polyvinylpyrrolidone (K-90), a polyamide resin and an epoxy in a solvent mixture of n-methylpyrrolidone, tetrahydrofuran, dimethylacetamide, ethanol and xylene. The coating was dried at 85° C. for 45 minutes. A coating containing bubbles was formed.

EXAMPLE 24

A large number of isocyanate-based coatings were made with varying concentrations of solvent and other components. For each of 47 samples, a wire was coated with a pre-coat and base coat as in Example 1. The wire was then dip coated in a solution containing the corresponding echogenic coating solvent mixture with or without added surfactant. The wire was then exposed to water for 10 minutes, then dried at 85° C. for 15 minutes. All coatings gave an echogenic response as compared to an uncoated wire which gave no echogenic response. This demonstrates the range of conditions at which the inventive method may be performed.

| | |
|---|---|
| A: isocyanate prepolymer, 20–30% | H: xylene, 0–20% |
| B: dimethylsulfoxide, 16–48% | I: ethyl acetate, 0–20% |
| C: tetrahydrofuran, 0–35% | J: dichloromethane, 0–32% |
| D: toluene, 0–30% | K: 1,1,1-trichloroethane, 0–16% |
| E: cyclohexanone, 0–32% | L: n-methylpyrrolidone, 0–20% |
| F: hexane, 0–16% | M: n-butyl acetate, 0–16% |
| G: 2-butanone, 0–20% | N: silicone surfactant, 0–2% |

EXAMPLE 25

A wire was coated with a precoat and base coat solution as in Example 1. The wire was then dip coated in a solution consisting of sodium bicarbonate (25% w/w), cellulose ester, an acrylic polymer, and a polyurethane resin dissolved in a mixture of solvents containing cyclohexanone, tetrahydrofuran, ethyl acetate, and benzyl alcohol. The wire was dried at 85° C. for 60 minutes. Next, the wire was immersed in glacial acetic acid and water. An echogenic surface was formed.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. An ultrasonically visible solid device for inserting into a target medium, the device comprising a surface and a matrix, wherein the surface has open gas-trapping structures capable of entrapping gas when the device is in the target medium, and/or the matrix comprises bubbles of a non-gas material that changes phase to gas when heated, the entrapped or heated gas causing the device to be ultrasonically visible.

2. A device according to claim 1, wherein the entrapped or heated gas provides an acoustic impedance mismatch of at least a factor of about 25.

3. A device according to claim 1 wherein the device is a medical or veterinary device.

4. A device according to claim 3, selected from the group consisting of a catheter, needle, stent, hydrocephalus shunt, draintube, pacemaker, dialysis device, small or temporary joint replacement, urinary sphincter, urinary dilator, long term urinary device, tissue bonding urinary device, penile prosthesis, vascular catheter port, peripherally insertable central venous catheter, long term tunneled central venous catheter, peripheral venous catheter, short term central venous catheter, arterial catheter, PCTA or PTA catheter, and pulmonary artery Swan-Ganz catheter, and combinations thereof.

5. A method of using the device of claim 3 comprising inserting the device into a tissue, directing an ultrasound beam at the tissue, and observing the device in the tissue.

6. A device according to claim 3, wherein the device is selected from the group consisting of a guidewire, a surgical instrument, endoscopy equipment, an angioplasty balloon, a wound drain, a gastroenteric tube, laparoscopy equipment, a pellet, and an implant.

7. A device according to claim 1, further comprising a contrast agent for non-ultrasound imaging.

8. A device according to claim 7, wherein the contrast agent is a contrast agent for x-ray or magnetic resonance imaging.

9. A method for increasing the echogenicity of an object when subjected to ultrasound in an ambient material, the method comprising the steps of:

providing a coating liquid comprising a film-forming constituent;

applying the coating liquid to the object;

allowing the film-forming constituent to form a film comprising a solid matrix; and providing the film with an echogenic structure presenting echogenicity-increasing gas/non-gas interfaces activatable when the object is in the ambient material.

10. The method of claim 9, wherein the echogenic structure comprises open gas-trapping structures.

11. The method of claim 10, wherein providing the film with an echogenic structure comprises including a reactive material in the coating liquid, and contacting the reactive material with a reactor to produce gas.

12. The method of claim 11, wherein the reactive material is a diisocyanate, the reactor is a hydrogen donor, and the gas is carbon dioxide.

13. The method of claim 12, wherein the diisocyanate is selected from the group consisting of toluene diisocyanate, methylene diphenylisocyanate and a diisocyanate prepolymer.

14. The method of claim 12, wherein the hydrogen donor is selected from the group consisting of water, alcohol, and amine in liquid or vapor state.

15. The method of claim 11, wherein the reactive material is a carbonate or bicarbonate salt, the reactor is an acid, and the gas is carbon dioxide.

16. The method of claim 11, wherein the reactive material is a diazo compound, the reactor is ultraviolet light, and the gas is nitrogen.

17. The method of claim 11, wherein the reactive material is a peroxide compound, the reactor is selected from the group consisting of an acid, a metal, thermal energy, and light, and the gas is oxygen.

18. The method of claim 11, wherein the gas is selected from the group consisting of chlorine, hydrogen chloride and other gas with a vapor pressure higher than air.

19. The method of claim 9, wherein the film-forming constituent is a reactive polymer-forming material, and the applying step comprises reacting the reactive polymer-forming material to produce a polymer matrix and gas.

20. The method of claim 9 wherein the step of providing the film with an echogenic structure comprises etching the coating by chemical or physical means to produce the echogenic features.

21. The method of claim 9, wherein the echogenic structure is produced by including in the coating a non-gas compound that changes phase to generate gas bubbles upon heating the object to a predetermined temperature.

22. The method of claim 9, further comprising agitating the coating liquid to produce bubbles.

23. The method of claim 22, wherein the agitating comprises sonicating or vortexing.

24. The method of claim 9, wherein the film-forming constituent id selected from the group consisting of albumin, carboxylic polymers, cellulose, cellulose derivatives, gelatin, polyacetates, polyacrylics, polyacrylamides, polyamides, polyvinylbutyrals, polycarbonates, polyethylenes, polysilanes, polyureas, polyurethanes, polyethers, polyesters, polyoxides, polystyrenes, polysulfides, polysulfones, polysulfonides, polyvinylhalides, pyrrolidones, rubbers, and thermal-setting polymers.

25. The method of claim 9, further comprising forming a precipitate in the solid matrix.

26. An echogenic object including an echogenic film produced by the method of claim 9.

27. A coating liquid for producing an echogenic layer on a substrate, comprising a liquid vehicle, a constituent that forms a coating when the coating liquid is applied to the substrate, and a means for providing activatable echogenic gas/non-gas interfaces at the surface of the coating.

28. A coating liquid according to claim 27, the interface-providing means being selected from the group consisting of gas bubbles in the coating liquid, a reactive material that generates gas upon reaction with a reactor, a non-gas material that changes phase to gas when heated, and a combination.

29. A coating liquid according to claim 28, wherein the reactive material is selected from the group consisting of a diisocyanate producing carbon dioxide upon reaction with a hydrogen donor, a carbonate or bicarbonate salt producing carbon dioxide upon reaction with an acid, a diazo compound producing nitrogen upon reaction with ultraviolet light, and a peroxide compound producing oxygen upon reaction with a reactor selected from the group consisting of an acid, a metal, thermal energy, and light.

30. A device according to claim 1, wherein the device comprises a substrate and a coating, the coating comprising the surface and the matrix.

31. A device according to claim 30, wherein the coating has a thickness between about 5 and about 50 microns.

32. A device according to claim 30, wherein the coating is obtained by a method comprising reacting isocyanate with water.

33. The device of claim 30, further comprising a pre-coat and/or a base coat applied to the substrate before the coating.

34. A device according to claim 1, wherein the surface has open gas-trapping structures capable of entrapping gas when the object is in the target medium.

35. A device according to claim 34 wherein the gas-trapping structures are selected from the group consisting of pores, channels, cavities, pockets, and combinations thereof.

36. A device according to claim 35 wherein the gas-trapping structures have a dimension selected from one of diameters or widths ranging between 0.1 micron and about 300 microns.

37. A device according to claim 35 wherein the gas-trapping structures have a dimension selected from one of diameters or widths ranging between 1 micron and about 50 microns.

38. A device according to claim 34, comprising gas entrapped on the surface of the device, the gas forming an interface with the target medium.

39. A device according to claim 34, wherein the gas is air.

40. The surface of claim 34, further comprising a top coat layer applied to the device, the top coat layer reducing the wettability of the open structures so as to promote and/or prolong the entrapment of gas.

41. A device according to claim 1, wherein the surface is smooth to the touch.

42. A device according to claim 1, wherein the matrix comprises a non-gas material that changes phase to gas when heated, the non-gas material being a liquid selected from the group consisting of perfluorocarbons, hydrocarbons, halogenated hydrocarbons, and other materials having a sufficiently high vapor pressure as to generate gas bubbles upon heating to a predetermined temperature.

43. A device according to claim 1, wherein the matrix comprises bubbles of a non-gas material that changes phase to gas when heated, the non-gas material being a solid compound having a sublimation pressure sufficient to generate bubbles upon heating to a predetermined temperature.

44. A device comprising a surface and means for trapping gas on the surface in a target medium and/or means for producing gas within the device upon heating, whereby the gas trapping means and/or gas producing means enhances echogenicity of the device when the device is placed in the target medium.

45. A method of visualizing a device when the device is placed in an ambient medium, comprising trapping gas at the surface of the device and/or heating the device to change a non-gas material contained within the device to gas, and:

inserting the device into an ambient medium, directing an ultrasound beam at the ambient medium while the gas is trapped and/or the device is heated, and observing the device in the ambient medium.

46. A method according to claim 45, wherein the ambient medium is a tissue.

47. A method according to claim 46, wherein the device is a medical device and the tissue is human tissue.

48. A method for increasing the echogenicity of an object when subjected to ultrasound in an ambient material, the method comprising steps for:

forming a film on the object; and rendering the film echogenic by providing the film with means for trapping gas at the surface of the object, and/or means for producing gas within the device upon heating, whereby the gas trapping means and/or gas producing means becomes ultrasonically active when the object is in the ambient material.

49. An ultrasonically visible solid device for inserting into a target medium, the device comprising a surface, wherein the surface has an echogenic structure presenting echogenicity increasing gas/non-gas interfaces activatable when the object is in the ambient material.

* * * * *

UNITED STATES PATENT AND TRADEMARK OFFICE
CERTIFICATE OF CORRECTION

PATENT NO. : 6,106,473
DATED : August 22, 2000
INVENTOR(S) : Violante et al.

It is certified that error appears in the above-identified patent and that said Letters Patent is hereby corrected as shown below:

Title page,
Item to read as follows:

-- [56] References Cited:

U.S. PATENT DOCUMENTS

| | | |
|---|---|---|
| 3,605,750 | 9/1971 | Sheridan et al. |
| 4,111,190 | 9/1978 | Plumridge |
| 4,276,885 | 7/1981 | Tickner et al. |
| 2,277,367 | 7/1981 | Madsen et al. |
| 4,322,164 | 3/1982 | Shaw et al. |
| 4,386,612 | 6/1983 | Röder et al. |
| 4,490,139 | 12/1984 | Huizenga et al. |
| 4,567,896 | 2/1986 | Barnea et al. |
| 4,572,203 | 2/1986 | Feinstein |
| 4,582,061 | 4/1986 | Fry |
| 4,681,119 | 7/1987 | Rasor et al. |
| 4,697,595 | 11/1987 | Breyer et al. |
| 4,709,703 | 12/1987 | Lazarow et al. |
| 4,718,433 | 1/1988 | Feinstein |
| 4,718,907 | 1/1988 | Karwoski et al. |
| 4,805,628 | 2/1989 | Fry et al. |
| 4,869,259 | 9/1989 | Elkins |
| 4,872,922 | 10/1989 | Bunker et al. |
| 4,911,172 | 3/1990 | Bui et al |
| 5,048,530 | 9/1991 | Hurwitz |
| 5,054,310 | 10/1991 | Flynn |
| 5,095,911 | 3/1992 | Pomeranz |
| 5,213,569 | 5/1993 | Davis |
| 5,219,335 | 6/1993 | Willard et al. |
| 5,221,269 | 6/1993 | Miller et al. |
| 5,289,831 | 3/1994 | Bosley |
| 5,333,613 | 8/1994 | Tickner et al. |
| 5,344,494 | 9/1994 | Davidson et al. |
| 5,383,466 | 1/1995 | Partika |
| 5,409,688 | 4/1995 | Quay |
| 5,454,373 | 10/1995 | Koger et al. |

UNITED STATES PATENT AND TRADEMARK OFFICE
CERTIFICATE OF CORRECTION

PATENT NO. : 6,106,473
DATED : August 22, 2000
INVENTOR(S) : Violante et al.

It is certified that error appears in the above-identified patent and that said Letters Patent is hereby corrected as shown below:

Continued:

| | | |
|---|---|---|
| 5,490,521 | 2/1996 | Davis et al. |
| 5,676,925 | 10/1997 | Klaveness et al. |
| 5,690,908 | 11/1997 | Deutsch |

FOREIGN PATENT DOCUMENTS

| | | |
|---|---|---|
| 94/16739 | 8/1994 | WIPO |
| 2 272 633 | 12/1975 | France |
| 3501355 A1 | 7/1985 | Germany |

OTHER PUBLICATIONS

M.R. Violante et al., "Particle-Stabilized Bubbles for Enhanced Organ Ultrasound Imaging", Investigative Radiology, Vol. 26, supp. 1, November 1991, pp. S194-S197.

Barbara A. Carroll et al., "Gelatin Encapsulated Nitrogen Micro-Bubbles as Ultrasound Contrast Agents", Investigative Radiology, Vol. 15, May-June 1980, pp. 260-266.

K.J. Parker et al., "A Particulate Contrast Agent with Potential for Ultrasound Imaging of Liver", Ultrasound in Med. & Biology, Vol. 13, No. 9, March 1987, pp. 555-566.

UNITED STATES PATENT AND TRADEMARK OFFICE
CERTIFICATE OF CORRECTION

PATENT NO. : 6,106,473
DATED : August 22, 2000
INVENTOR(S) : Violante et al.

It is certified that error appears in the above-identified patent and that said Letters Patent is hereby corrected as shown below:

Jonathan Ophis et al., "Contrast Agents in Diagnostic Ultrasound", *Ultrasound in Med. & Biology,* Vol. 15, No. 4, 1989, pp. 319-333.

Signed and Sealed this

Thirteenth Day of November, 2001

Attest:

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO. : 6,106,473
DATED : August 22, 2000
INVENTOR(S) : Violante et al.

It is certified that error appears in the above-identified patent and that said Letters Patent is hereby corrected as shown below:

<u>Title page,</u>
Item [56], References Cited, add the following references:

U.S. PATENT DOCUMENTS

| | | |
|---|---|---|
| 3,605,750 | 9/1971 | Sheridan et al. |
| 4,111,190 | 9/1978 | Plumridge |
| 4,276,885 | 7/1981 | Tickner et al. |
| 2,277,367 | 7/1981 | Madsen et al. |
| 4,322,164 | 3/1982 | Shaw et al. |
| 4,386,612 | 6/1983 | Röder et al. |
| 4,490,139 | 12/1984 | Huizenga et al. |
| 4,567,896 | 2/1986 | Barnea et al. |
| 4,572,203 | 2/1986 | Feinstein |
| 4,582,061 | 4/1986 | Fry |
| 4,681,119 | 7/1987 | Rasor et al. |
| 4,697,595 | 11/1987 | Breyer et al. |
| 4,709,703 | 12/1987 | Lazarow et al. |
| 4,718,433 | 1/1988 | Feinstein |
| 4,718,907 | 1/1988 | Karwoski et al. |
| 4,805,628 | 2/1989 | Fry et al. |
| 4,869,259 | 9/1989 | Elkins |
| 4,872,922 | 10/1989 | Bunker et al. |
| 4,911,172 | 3/1990 | Bui et al |
| 5,048,530 | 9/1991 | Hurwitz |
| 5,054,310 | 10/1991 | Flynn |
| 5,095,911 | 3/1992 | Pomeranz |
| 5,213,569 | 5/1993 | Davis |
| 5,219,335 | 6/1993 | Willard et al. |
| 5,221,269 | 6/1993 | Miller et al. |
| 5,289,831 | 3/1994 | Bosley |
| 5,333,613 | 8/1994 | Tickner et al. |
| 5,344,494 | 9/1994 | Davidson et al. |
| 5,383,466 | 1/1995 | Partika |
| 5,409,688 | 4/1995 | Quay |
| 5,454,373 | 10/1995 | Koger et al. |
| 5,490,521 | 2/1996 | Davis et al. |
| 5,676,925 | 10/1997 | Klaveness et al. |
| 5,690,908 | 11/1997 | Deutsch |

UNITED STATES PATENT AND TRADEMARK OFFICE
CERTIFICATE OF CORRECTION

PATENT NO.    : 6,106,473
DATED         : August 22, 2000
INVENTOR(S)   : Violante et al.

It is certified that error appears in the above-identified patent and that said Letters Patent is hereby corrected as shown below:

FOREIGN PATENT DOCUMENTS

| | | |
|---|---|---|
| 94/16739 | 8/1994 | WIPO |
| 2 272 633 | 12/1975 | France |
| 3501355 A1 | 7/1985 | Germany |

OTHER PUBLICATIONS

M.R. Violante et al., "Particle-Stabilized Bubbles for Enhanced Organ Ultrasound Imaging", Investigative Radiology, Vol. 26, supp. 1, November 1991, pp. S194-S197.

Barbara A. Carroll et al., "Gelatin Encapsulated Nitrogen Micro-Bubbles as Ultrasound Contrast Agents", Investigative Radiology, Vol. 15, May-June 1980, pp. 260-266.

K.J. Parker et al., "A Particulate Contrast Agent with Potential for Ultrasound Imaging of Liver", Ultrasound in Med. & Biology, Vol. 13, No. 9, March 1987, pp. 555-566.

Jonathan Ophis et al., "Contrast Agents in Diagnostic Ultrasound", Ultrasound in Med. & Biology, Vol. 15, No. 4, 1989, pp. 319-333.

This certificate supersedes Certificate of Correction issued November 13, 2001.

Signed and Sealed this

Fifth Day of November, 2002

*Attest:*

*Attesting Officer*

JAMES E. ROGAN
*Director of the United States Patent and Trademark Office*